(12) United States Patent
Keller et al.

(10) Patent No.: US 11,998,377 B2
(45) Date of Patent: Jun. 4, 2024

(54) AIR COOLED PET SCANNER GANTRY

(71) Applicant: Siemens Medical Solutions USA, Inc., Malvern, PA (US)

(72) Inventors: John Keller, Knoxville, TN (US); James L. Corbeil, Knoxville, TN (US); Ziad Burbar, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 263 days.

(21) Appl. No.: 17/757,152

(22) PCT Filed: May 19, 2020

(86) PCT No.: PCT/US2020/070061
§ 371 (c)(1),
(2) Date: Jun. 10, 2022

(87) PCT Pub. No.: WO2021/236172
PCT Pub. Date: Nov. 25, 2021

(65) Prior Publication Data
US 2022/0409155 A1    Dec. 29, 2022

(51) Int. Cl.
*A61B 6/00*  (2024.01)
*A61B 6/03*  (2006.01)
*A61B 6/42*  (2024.01)

(52) U.S. Cl.
CPC ............ *A61B 6/4488* (2013.01); *A61B 6/037* (2013.01); *A61B 6/4258* (2013.01)

(58) Field of Classification Search
CPC ..... A61B 6/4258; A61B 6/4488; A61B 6/037; A61B 6/4417; A61B 6/035; A61B 6/5235; A61B 6/032; A61B 6/4435; A61B 6/4447; A61B 5/055; A61B 6/4266; A61B 6/463; G01T 1/2985; G01T 1/244; G01T 1/1648; G01T 1/249; H01L 31/024; G01J 5/061;

(Continued)

(56) References Cited

U.S. PATENT DOCUMENTS 10,353,084 B1    7/2019   Wagner et al.
2004/0228450 A1  11/2004  Mueller et al.
(Continued)

FOREIGN PATENT DOCUMENTS

CN    103860187    6/2014
EP    3466489      4/2019
(Continued)

OTHER PUBLICATIONS

International Search Report for Corresponding PCT Application No. PCT/US2021/070061, received Feb. 15, 2021.

*Primary Examiner* — Irakli Kiknadze (57) ABSTRACT

Provided is a PET scanner system having a PET scanner gantry that is configured for delivering a uniformly distributed cooling air to a plurality of detectors housed in the PET scanner gantry. The PET scanner gantry includes a cooling air delivery manifold that includes a patient tunnel portion; and a front funnel portion. The front funnel portion includes an annular interior wall defining an entry opening of the patient tunnel portion; and an air plenum has an annular structure for carrying a flow of pressurized cooling air received from a remote source supplements the pressurized cooling air with a supply of ambient air and directs it to the plurality of detectors.

33 Claims, 7 Drawing Sheets

(58) Field of Classification Search
CPC .... A61N 5/1049; A61N 5/1081; A61N 5/103; A61N 2005/005; G01R 33/4808; G01R 33/3804; H05G 1/025; H05G 1/02; G01N 23/046
USPC ......................................................... 378/199
See application file for complete search history.

(56) References Cited

U.S. PATENT DOCUMENTS

| | | | |
|---|---|---|---|
| 2007/0053501 | A1 | 3/2007 | Distler et al. |
| 2010/0266096 | A1 | 10/2010 | Sharpless |
| 2013/0119259 | A1 | 5/2013 | Martin et al. |
| 2017/0059720 | A1* | 3/2017 | McBroom ............ G01T 1/20188 |
| 2017/0176607 | A1 | 6/2017 | Liu et al. |
| 2018/0095182 | A1* | 4/2018 | Su ........................... A61B 6/037 |
| 2021/0208294 | A1* | 7/2021 | Wu ........................... G01T 1/202 |
| 2022/0342096 | A1* | 10/2022 | Wu ........................ A61B 6/4488 |

FOREIGN PATENT DOCUMENTS

| | | |
|---|---|---|
| JP | H10160847 | 6/1998 |
| JP | 2004283577 | 10/2004 |
| JP | 2005161059 | 6/2005 |
| JP | 2007319670 | 12/2007 |

* cited by examiner

AIR COOLED PET SCANNER GANTRY

FIELD

The present disclosure generally relates to a novel configuration for a PET or a PET/CT scanner gantry that improves cooling of the PET detector electronic assembly.

BACKGROUND

Medical imaging devices in which the patient is positioned within a tunnel, such as PET and PET/CT scanners, require cooling that is typically accomplished with application of one or more cooling medium. Such cooling medium can be a liquid, gas, or a combination of both. The presence of the tunnel for the patient within the imaging volume greatly limits the placement of the components such as gamma detectors in the PET scanners to radial arrangement around the tunnel. The operational effects of the cooling system on the patient comfort must be considered. For example, in the existing PET and PET/CT scanner systems, the noise generated by the cooling system can be undesirably loud.

Often, individual electronic components such as the gamma detector assembly are employed with their own cooling means and/or are ganged together in such a manner as to share a common stream of cooling medium with great difficulty because of the aforementioned limitation in space and patient comfort.

The gamma detector assembly includes electronic components such as SiPM detectors and their associated drivers. All these electronic components generate heat while operating and the components must be cooled to maintain optimal performance because overheating can detrimentally affect their performance. Therefore, in conventional PET and PET/CT scanner systems, the electronic components typically have their own source of cooling air. The cooling air source must be both uniformly distributed and reliable so that overheating conditions do not occur, or heating related errors exhibited by the electronic components must be compensated. Often, however, these design elements are in conflict with one another.

In the conventional PET or PET/CT scanners, a cooling fan or multiple cooling fans are packaged within the gantry that houses the gamma detectors to ensure the performance of the gamma detectors and other electronics therein. This assurance, however, comes with a cost. Each cooling fan pushes the noise level towards a maximum threshold and if an array of gamma detectors is to work in unison, any detector not working properly, such as by a malfunctioning fan, brings the entire system down. With high number of fan units, the statistical likelihood of a system failure is stacked against the assurance of a reliable design. Thus, a system incorporating multiple cooling fans has hidden costs associated with system downtime, service, component replacement, and patient discomfort due to noise. Conversely, distributing the cooling airflow using just one or a few fans equally around the PET gantry can be difficult to realize when accounting for the loss of gantry volume, especially as the airflow must be balanced and stable. The cost of a liquid cooling system is even higher, with failure leading to catastrophic results. Therefore, an improved cooling system for PET or PET/CT scanner.

SUMMARY

In one aspect, a PET scanner gantry incorporating a cooling air delivery manifold according to the present disclosure is disclosed. The air delivery manifold comprises a patient tunnel portion, a front funnel portion, and a plurality of gamma detectors housed inside the PET scanner gantry and positioned behind the front funnel portion. The front funnel portion comprises an annular interior wall defining an entry opening of the patient tunnel portion; and an air plenum comprising an annular structure for carrying a flow of pressurized air received from a remote source. The air plenum comprises an annular nozzle configured for directing the flow of pressurized air toward the plurality of gamma detectors. The air plenum also comprises a supplemental air inlet that draws additional air from the ambient air and merges it with the primary pressurized cooling air flowing out of the annular nozzle as high-velocity air.

A PET scanner system fitted with the PET scanner gantry is also disclosed.

BRIEF DESCRIPTION OF THE DRAWINGS

The features of the embodiments described herein will be more fully disclosed in the following detailed description, which is to be considered together with the accompanying drawings wherein like numbers refer to like parts. All drawing figures are schematic and they are not intended to represent actual dimensions of the structures or relative ratios of their dimensions.

DETAILED DESCRIPTION

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

Disclosed herein is a cooling air delivery manifold concept that assimilates the cooling air delivery manifold into a cover set of a gantry of a PET scanner or a PET/CT hybrid scanner. For the purposes of discussion, the term "PET scanner" will be used herein as referring to both PET scanner and PET/CT hybrid scanner embodiments.

More specifically, the cooling air delivery manifold is assimilated into the front funnel portion of the patient tunnel of the PET scanner gantry. The cooling air delivery manifold is configured such that it is not restricted by the existence of a bore nor by other radial constraints. The cooling air delivery manifold is configured to receive a supply of pressurized cooling air from one or more remote source and uniformly deliver the cooling air to the gamma detectors in the gantry by utilizing an airfoil shape that has been incorporated in to the cooling air delivery manifold.

Figure 1:
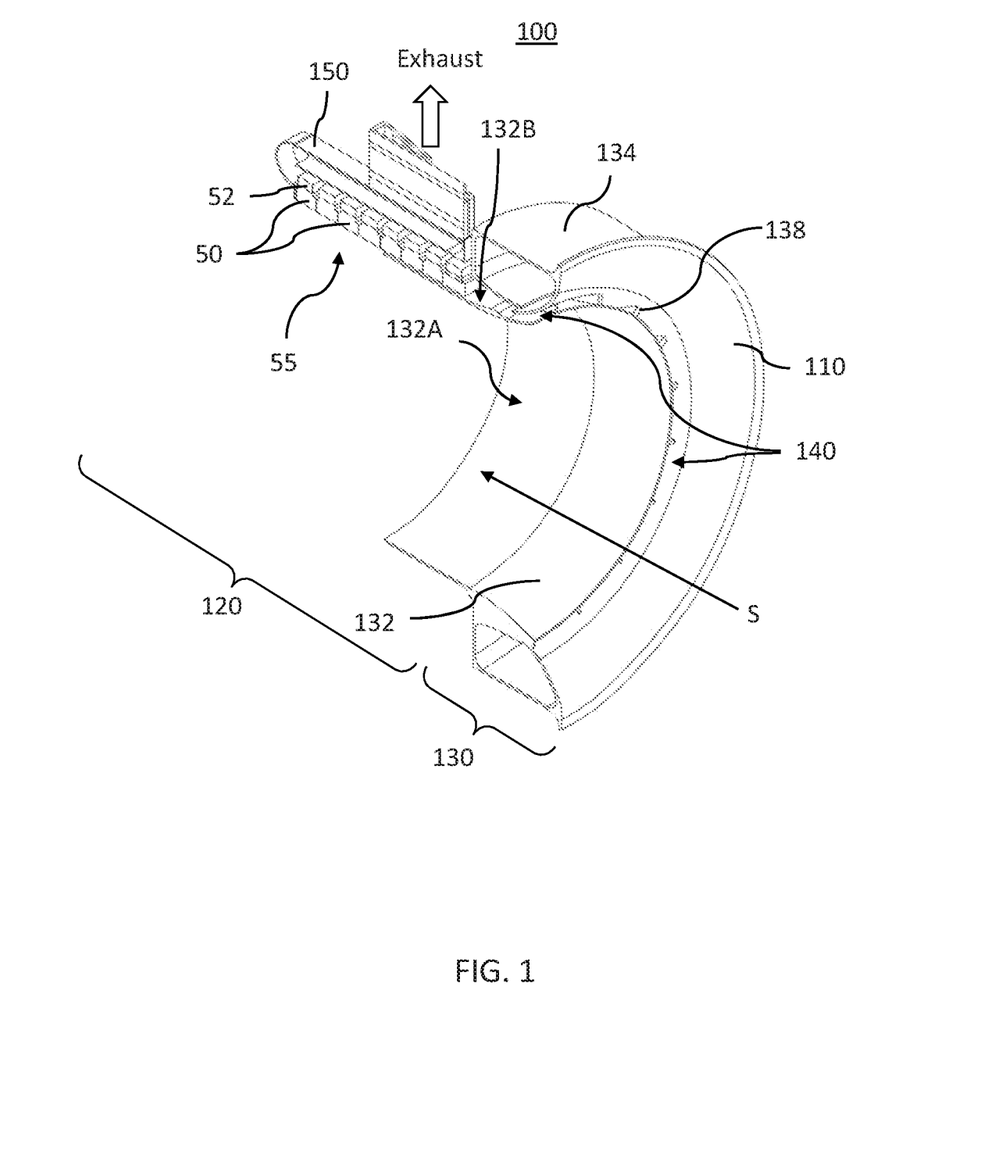
FIG. 1 is a cross-sectioned view illustration of a PET scanner gantry that incorporates a cooling air delivery manifold of the present disclosure.
Figure 2:
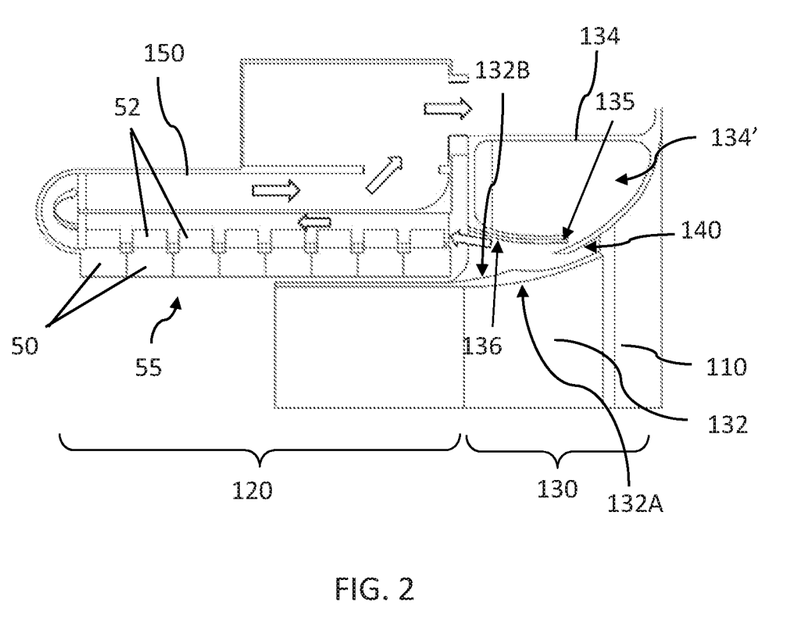
FIG. 2 is a cross-sectional view of a portion of the PET scanner gantry of FIG. 1.
Figure 3:
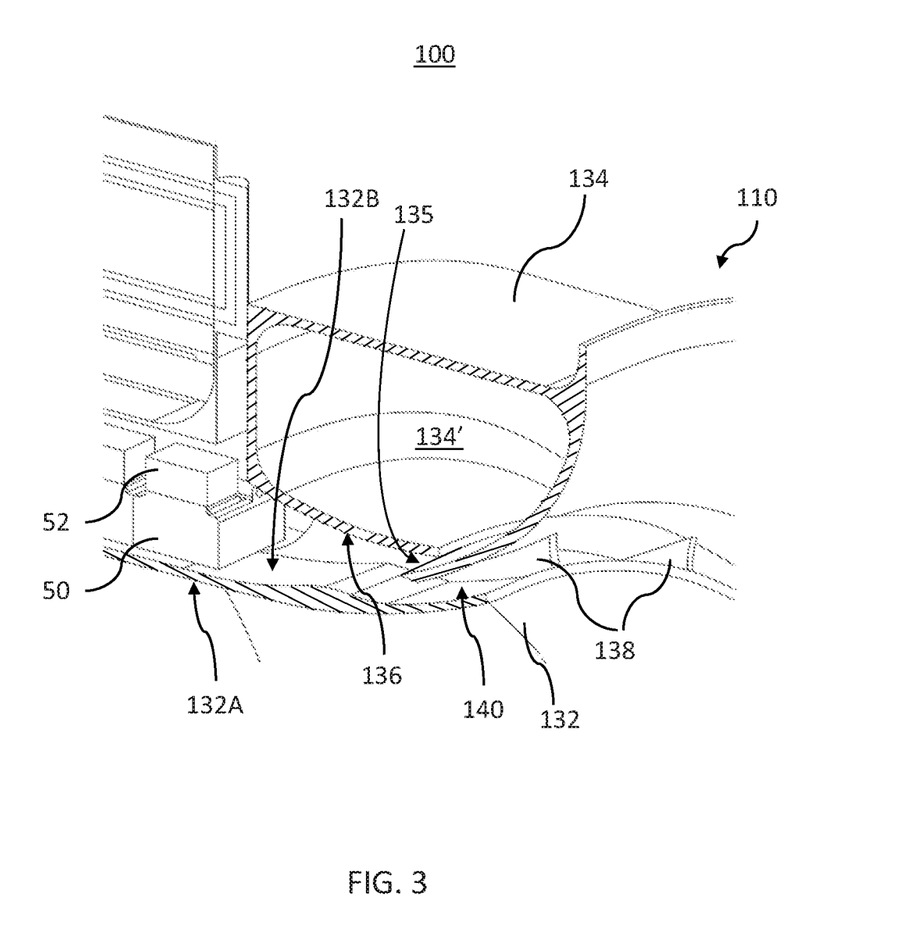
FIG. 3 is a detailed perspective view of the cross-sectioned portion shown in FIG. 2.

Referring to FIGS. 1-3, a PET scanner gantry 100 incorporating a cooling air delivery manifold 110 according to the present disclosure is disclosed. The air delivery manifold 110 comprises a patient tunnel portion 120, a front funnel portion 130, and a plurality of gamma detectors 50 housed inside the PET scanner gantry 100 and positioned behind the front funnel portion 130. The front funnel portion 130 comprises an annular interior wall 132 defining an entry opening of the patient tunnel portion 120; and an air plenum 134 comprising an annular cavity structure for carrying a flow of pressurized air received from one or more remote source (not shown). The annular cavity structure of the air plenum 134 has an interior space 134' that carries the flow of pressurized air. The annular cavity structure of the air plenum 134 in one embodiment can also be described as having a substantially toroid shape. The illustration in FIG. 1 is a cross-sectioned view of the PET scanner gantry 100 and shows about half of the annular cavity structure of the air plenum 134.

One benefit of the cooling air delivery manifold 110 of the present disclosure is that it allows the one or more sources of the pressurized cooling air, i.e., the hardware such as fans or impellers that provide the supply of pressurized cooling air, to be located remote from the PET scanner system so that the patient in the PET scanner can be insulated from the noise of such hardware.

The air plenum 134 comprises an annular nozzle 135 configured for directing the flow of pressurized cooling air from the interior space 134' toward the plurality of gamma detectors 50. The air nozzle 135 can be better seen in the more detailed views in FIGS. 2 and 3. Each of the discrete detector in the array of gamma detectors 50 have one or more heatsinks 52 attached to it to cool the detector.

The air plenum 134 further comprises an airfoil surface 136 located adjacent to and downstream of the annular nozzle 135. In some embodiments of the air delivery manifold 110, the annular nozzle 135 is divided into a series of non-continuous slots by a plurality of fins 138 provided at regular intervals along the annular structure of the air plenum 134. The plurality of fins 138 can be better seen in FIGS. 1 and 3. The plurality of fins 138 are oriented parallel to the longitudinal axis of the patient tunnel portion 120 so that the pressurized cooling air exiting each of the non-continuous slots in the annular nozzle 135 is directed toward the gamma detectors 50 in detector electronic assembly (DEA) 55. Additionally, dividing the annular nozzle 135 into a series of non-continuous slots helps with maintaining balanced radially uniform flow of the cooling air around the circumference of the front funnel portion 130. For illustrative purpose, only one DEA 55 is depicted in FIG. 1. In an actual PET scanner gantry 100, however, a plurality of such DEA 55 are arranged circumferentially around the exterior of a first annular surface 132A forming detector rings.

The annular interior wall 132 is nested inside the annular structure of the air plenum 134, whereby a supplemental air inlet 140 is formed between the annular interior wall 132 and the air plenum 134, whereby when the pressurized air flows out of the annular nozzle 135, ambient air is drawn through the supplemental air inlet 140 and merges with the pressurized air exiting the annular nozzle 135 and flows toward the plurality of gamma detectors 50. The details of this phenomenon is discussed in more detail below.

As can be seen in FIG. 1, the plurality of fins 138 also connect the air plenum 134 to the annular interior wall 132. The plurality of fins 138 maintain a desired spacing between the air plenum 134 and the annular interior wall 132 which forms the supplemental air inlet 140. The provision of the plurality of fins 138 is applicable to all of the embodiments of the PET scanner gantry 100 and PET scanner system disclosed herein.

The plurality of fins 138 also provides the function of supporting the air plenum 134 under high pressure of the pressurized cooling air filling the interior space 134' by providing structural rigidity to the air plenum. Because the air plenum 134 is essentially a curved tube that has a disconnected side wall formed by the annular nozzle 135, without the support structure such as the fins 138 holding the edges of the annular nozzle 135 in place and preventing them from bursting outward from the pressure of the pressurized cooling air, the air plenum 134 may not hold its shape.

The annular interior wall 132 comprises a first annular surface 132A facing the tunnel space S defined by the patient tunnel portion 120 and a second annular surface 132B facing the air plenum.

Figure 4:
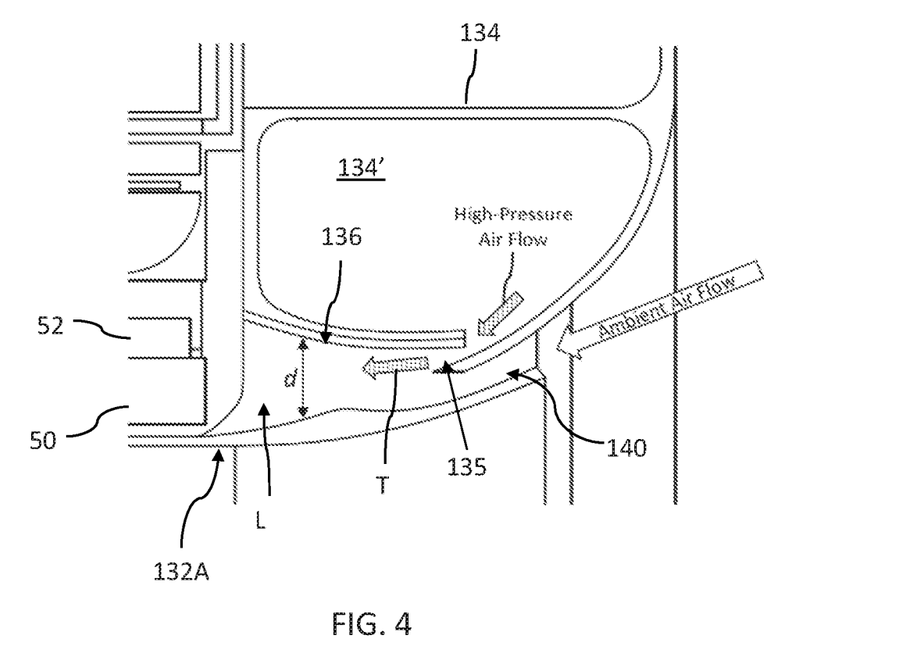
FIG. 4 is a detailed illustration of the cross-sectioned portion shown in FIG. 2, noting the flow of the cooling air according to the present disclosure.

Referring to FIG. 4, the airfoil surface 136 is contoured such that the surface falls away from the trajectory T of the high-velocity pressure driven air exiting the annular nozzle 135. Thus the distance d between the airfoil surface 136 and the second annular surface 132B of the annular interior wall 132 increases away from the annular nozzle 135. Thus, the volume of space between the airfoil surface 136 and the annular interior wall 132 increases in the direction toward the gamma detectors 50. Additionally, as the pressurized cooling air exits the annular nozzle 135, the contour of the airfoil surface 136 causes the high-velocity air exiting the annular nozzle 135 to hug the airfoil surface 136 and skim the airfoil surface 136 as it flows away from the annular nozzle 135 and toward the gamma detectors 50. As a result of this configuration, as the high-velocity pressure driven cooling air exits the annular nozzle 135 and skims along the airfoil surface 136, the air expands in volume, producing a low pressure area L between the airfoil surface 136 and the second annular surface 132B because of the inertance principle. This low pressure area L creates a suction that draws in the ambient air through the supplemental air inlet 140. The additional air drawn in from the ambient through the supplemental air inlet 140 joins the flow of the high-velocity cooling air, thus, amplifying the total amount of cooling air directed to the gamma detectors 50. Because this process of adding additional air is accomplished without any additional moving hardware such as fans or impellers, there is no additional noise generated while increasing the volume of cooling air flow. The airfoil surface 136 feature provided on the air plenum 134 is applicable to all of the embodiments of the PET scanner gantry 100 and PET scanner system disclosed herein.

Figure 5:
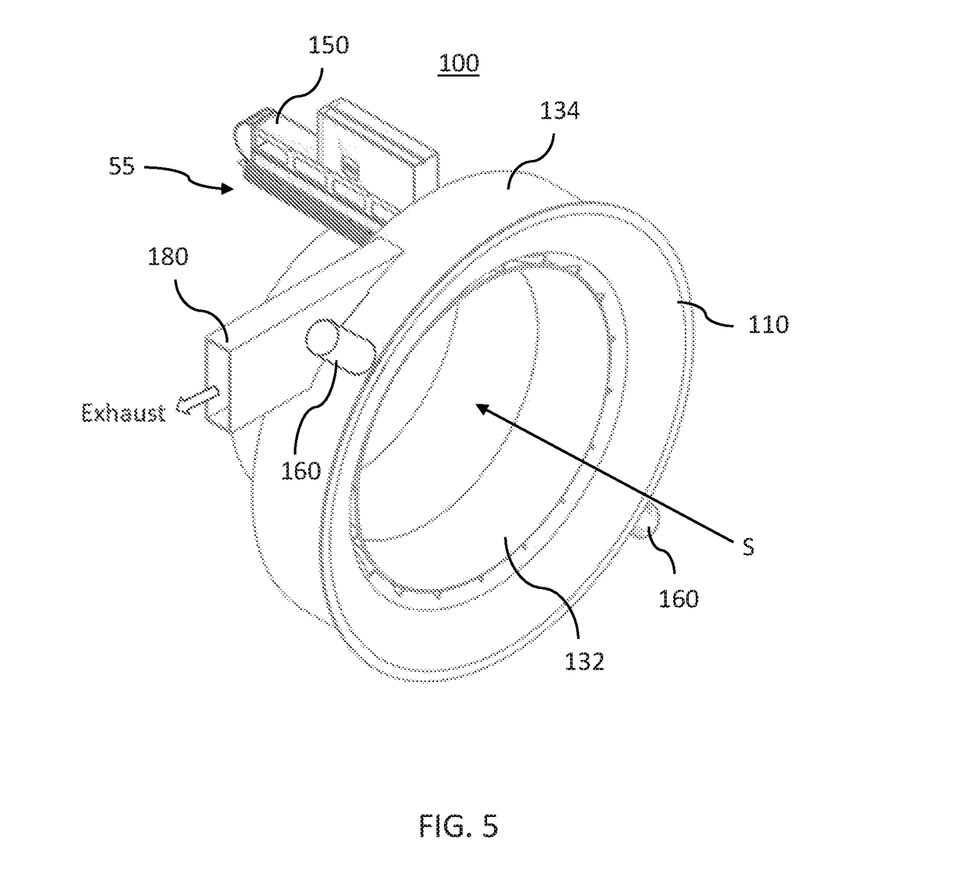
FIG. 5 is an illustration of the cooling air delivery manifold according to another embodiment of the present disclosure that incorporates guided exhaust air outlet.

The cooling air can be provided from a remote source to the air plenum 134. In some embodiments, the remote source for the cooling air can be located at some distance away from the PET scanner to minimize the noise to a patient that would be positioned in the scanner tunnel. In some preferred embodiment, the remote source can be located in a different room from the PET scanner to minimize the noise at the PET scanner for the patient's comfort. The remote source of cooling air can be pressurized plant air, sometimes referred to as facilities air, in which case the air plenum 134 just need to be connected to the plant air ducting. The remote source can be one or more fans or impellers that are appropriately configured to provide a desired amount of the cooling air to the air plenum 134. In some embodiments, the remote source for the cooling air can be one or more fans or impellers located on or around the gantry structure. In such embodiments, appropriate sound proofing packaging can be provided for the remote source for the cooling air to muffle and minimize the noise produced by the remote source. The air plenum 134 can comprise one or more air inlets 160 for receiving the flow of pressurized air from the remote source. FIG. 5 shows an embodiment of the PET scanner gantry 100 of the present disclosure that has two such air inlets 160 as an example.

In some embodiments of the cooling air delivery manifold 110, a plurality of sources for the pressurized cooling air supply can be connected to the air inlet 160 of the air plenum 134. As mentioned above, some examples of the sources for the pressurized cooling air supply can be fan(s) or impeller(s). Having multiple sources for the pressurized air provides redundancy which can provide improved reliability of the system. Additionally, when there are multiple sources for the pressurized air, the fans in the individual air source can run at lower speed, thus reducing the amount of noise generated.

Figure 6:
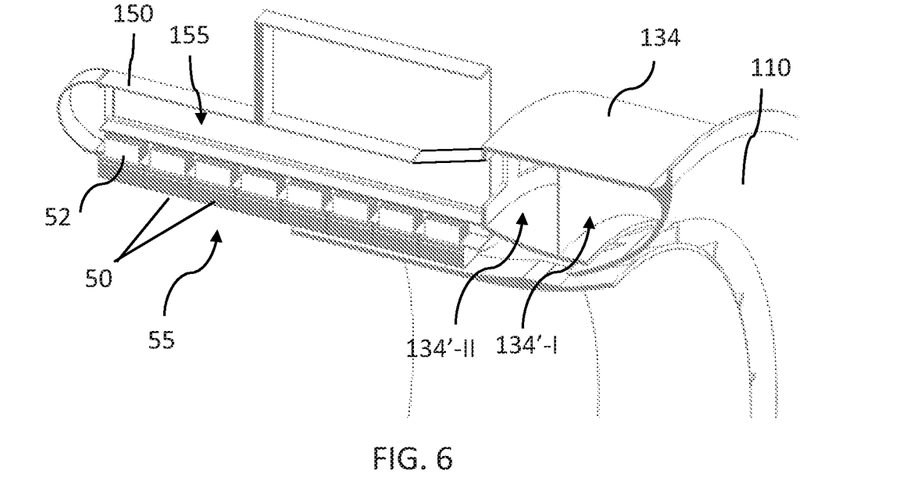
FIGS. 6-7 are cross-sectioned views of the embodiment of the cooling air delivery manifold of FIG. 5 showing the interior structures.
Figure 7:
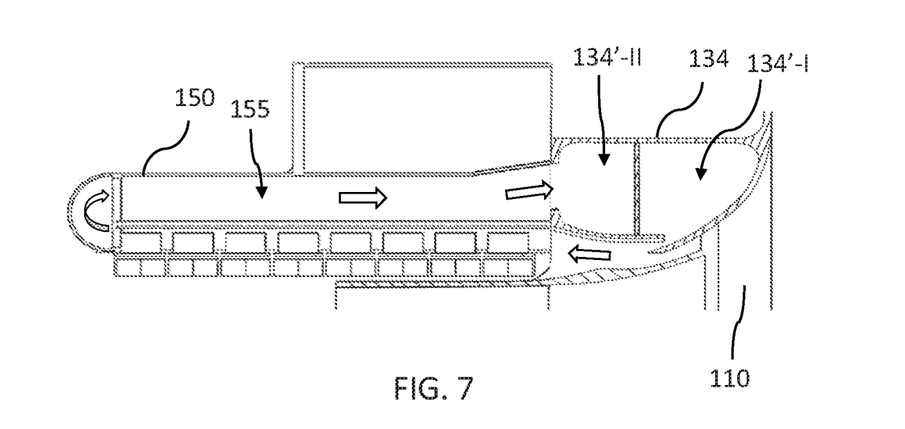

In the embodiments discussed above in connection with FIGS. 1-4, after the cooling air supplied by the air plenum 134 travels over the detector electronic components in the DEA 55, housing 150 can direct the now heated exhaust air to the ambient surrounding. This is shown in FIGS. 1 and 2. Referring to FIGS. 5-7, in some other embodiments, the air plenum 134 can be configured to incorporate a guided exhaust duct 134'-II that can direct the heated exhaust air away from the PET scanner via an exhaust outlet 180. An example of such exhaust outlet 180 is shown in FIG. 5.

As shown in the sectional views in FIGS. 6 and 7, in this embodiment, the interior space 134' of the air plenum 134 is divided into two main sections, the cooling air duct portion 134'-I that is configured to deliver the pressurized air for cooling, and the exhaust air duct portion 134'-II that is configured to direct the flow of heated exhaust air away from the PET scanner via the exhaust outlet 180. The exhaust air duct portion 134'-II receives a flow of exhaust air and directs the exhaust air away from the medical image scanner, wherein The flow of heated exhaust air is the cooling air flow after the cooling air flow has flown over the plurality of gamma detectors and returned to the air plenum 134 by the DEA housing 155.

Figure 8A:
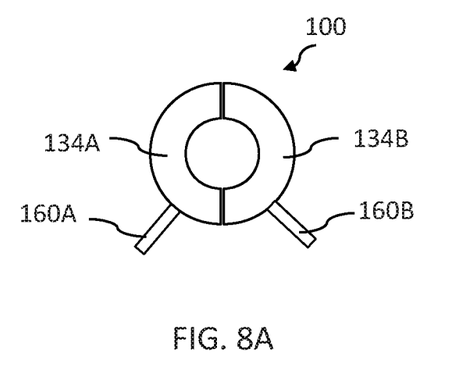
FIGS. 8A-8C are illustrations showing embodiments of cooling air delivery manifolds comprising an assembly of two or more air plenums according to the present disclosure.
Figure 8B:
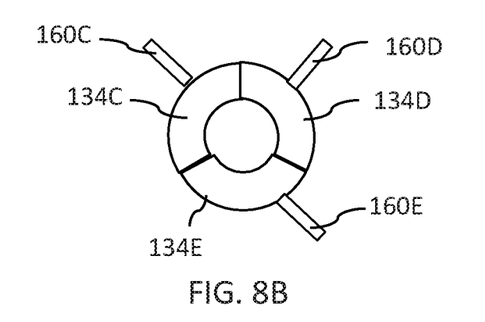
Figure 8C:
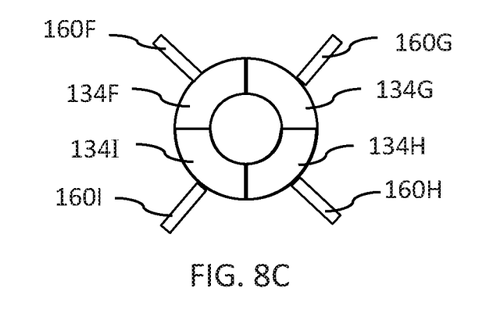

In some embodiments of the cooling air delivery manifold 110, air delivery manifold can comprise an assembly of more than one unconnected air plenums. For example, as shown in FIG. 8A, the cooling air delivery manifold 110 can be comprised of two air plenums 134A and 134B. As shown in FIG. 8B, the cooling air delivery manifold 110 can be comprised of three air plenums 134C, 134D, and 134E. As shown in FIG. 8C, the cooling air delivery manifold 110 can be comprised of four air plenums 134F, 134G, 134H, and 134I. In these embodiments, each of the more than one air plenums 134A, 134B, . . . are structured like the air plenum 134 shown in FIGS. 1-4 in terms of the cross-sectional shape of the air plenum 134 and the associated structures such as the annular nozzle 135, the airfoil surface 136, annular interior wall 132, supplemental air inlet 140, etc. that enable the cooling air flow directed to the plurality of gamma detectors 50. In the embodiments illustrated in FIGS. 8A-8C, each of the air plenums 134A-134I can comprise at least one air inlet 160A-160I, respectively. These multiple unconnected air plenums can each be configured to have both cooling air duct and exhaust air duct within each of the air plenum similar to the embodiment shown in FIGS. 6-7. Each of the air plenums 134A-134I would comprise an air inlet and an air outlet.

In the embodiments where the air delivery manifold 110 is configured as an assembly of more than one unconnected air plenums, each air plenum has a volume of interior space and each air plenum comprises one or more air inlet Air-in that is connected to a source for the pressurized cooling air. Depending on the needs of the particular application, each of the more than one air plenums can be connected to its own supply source for the pressurized cooling air or they can share one supply source for the pressurized cooling air.

According to another aspect, a PET scanner system that is fitted with the PET scanner gantry 100 incorporating a cooling air delivery manifold 110 according to the present disclosure is disclosed.

Compared to the conventional PET scanner detector cooling systems, in which the array of gamma detectors with the associated detector electronic assemblies on the detector rings are often provided with an array of cooling fans, the cooling air delivery manifold 110 provides a system that is less noisy and more reliable.

It will be understood that the foregoing description is of exemplary embodiments of this invention, and that the invention is not limited to the specific forms shown. Modifications may be made in the design and arrangement of the elements without departing from the scope of the invention.

We claim:

1. A medical image scanner gantry comprising:
    cooling air delivery manifold comprising:
        a patient tunnel portion; and
        a front funnel portion;
    a plurality of gamma detectors housed inside the medical image scanner gantry and positioned behind the front funnel portion that comprises:
        an annular interior wall defining an entry opening of the patient tunnel portion; and
        an air plenum comprising an annular structure for carrying a flow of pressurized air received from a remote source, wherein the air plenum comprising an annular nozzle configured for directing the flow of pressurized air toward the plurality of gamma detectors as a flow of high-velocity air for cooling the plurality of gamma detectors and their associated electronic components;
        wherein the annular interior wall is nested inside the annular structure of the air plenum, whereby a supplemental air inlet is formed between the annular interior wall and the air plenum, whereby when the flow of high-velocity air flows out of the annular nozzle, ambient air is drawn through the supplemental air inlet and merges with the flow of high-velocity air exiting the annular nozzle and flows toward the plurality of gamma detectors as cooling air flow.

2. The medical image scanner gantry of claim 1, wherein the air plenum further comprises an airfoil surface located adjacent to and downstream of the annular nozzle for directing the flow of high-velocity air toward the detectors.

3. The medical image scanner gantry of claim 2, further comprising a plurality of fins connecting the air plenum to the annular interior wall.

4. The medical image scanner gantry of claim 3, wherein the plurality of fins maintain a desired spacing between the air plenum and the annular interior wall which forms the supplemental air inlet.

5. The medical image scanner gantry of claim 2, wherein the air plenum comprises an air inlet for receiving the flow of pressurized air from a remote source.

6. The medical image scanner gantry of claim 1, further comprising a plurality of fins connecting the air plenum to the annular interior wall.

7. The medical image scanner gantry of claim 6, wherein the plurality of fins maintain a desired spacing between the air plenum and the annular interior wall which forms the supplemental air inlet.

8. The medical image scanner gantry of claim 1, wherein the air plenum comprises an air inlet for receiving the flow of pressurized air from a remote source.

9. The medical image scanner gantry of claim 1, wherein the annular interior wall comprises a first annular surface facing the opening of the patient tunnel portion and a second annular surface facing the air plenum and further comprising an annular ridge provided on the second annular surface and located downstream of the annular nozzle.

10. The medical image scanner gantry of claim 1, wherein the air plenum comprises:
   a cooling air duct portion for carrying the flow of pressurized air, wherein the cooling air duct portion includes the annular nozzle; and
   an exhaust air duct portion for receiving a flow of exhaust air and directing the exhaust air away from the medical image scanner, wherein the flow of exhaust air is said cooling air flow after said cooling air flow has flown over the plurality of gamma detectors.

11. A medical image scanner gantry comprising:
cooling air delivery manifold comprising:
   a patient tunnel portion; and
   a front funnel portion;
a plurality of gamma detectors housed inside the medical image scanner gantry and positioned behind the front funnel portion that comprises:
   an annular interior wall defining an entry opening of the patient tunnel portion; and
   an assembly of two or more air plenums, wherein each of the two or more air plenums has a curved structure that together form an annular assembly, wherein each of the two or more air plenums comprising a structure for carrying a flow of pressurized air received from a remote source, wherein each of the two or more air plenums comprising a curved nozzle configured for directing the flow of pressurized air toward the plurality of gamma detectors as a flow of high-velocity air for cooling the plurality of gamma detectors and their associated electronic components;
   wherein the annular interior wall is nested inside the annular assembly formed by the two or more air plenums, whereby a supplemental air inlet is formed between the annular interior wall and the two or more air plenums, whereby when the flow of high-velocity air flows out of the curved nozzles, ambient air is drawn through the supplemental air inlet and merges with the flow of high-velocity air exiting the curved nozzles and flows toward the plurality of gamma detectors as cooling air flow.

12. The medical image scanner gantry of claim 11, wherein each of the two or more air plenums further comprises an airfoil surface located adjacent to and downstream of the curved nozzle for directing the flow of high-velocity air toward the detectors.

13. The medical image scanner gantry of claim 11, further comprising a plurality of fins connecting the two or more air plenums to the annular interior wall.

14. The medical image scanner gantry of claim 11, wherein each of the two or more air plenums comprises:
   a cooling air duct portion for carrying the flow of pressurized air, wherein the cooling air duct portion includes the curved nozzle; and
   an exhaust air duct portion for receiving a flow of exhaust air and directing the exhaust air away from the medical image scanner, wherein the flow of exhaust air is said cooling air flow after said cooling air flow has flown over the plurality of gamma detectors.

15. A medical image scanner system comprising:
a medical image scanner gantry comprising:
   cooling air delivery manifold comprising:
      a patient tunnel portion; and
      a front funnel portion;
   a plurality of gamma detectors housed inside the medical image scanner gantry and positioned behind the front funnel portion that comprises:
      an annular interior wall defining an entry opening of the patient tunnel portion; and
      an air plenum comprising an annular structure for carrying a flow of pressurized air received from a remote source, wherein the air plenum comprising an annular nozzle configured for directing the flow of pressurized air toward the plurality of gamma detectors as a flow of high-velocity air for cooling the plurality of gamma detectors and their associated electronic components;
   wherein the annular interior wall is nested inside the annular structure of the air plenum, whereby a supplemental air inlet is formed between the annular interior wall and the air plenum, whereby when the flow of high-velocity air flows out of the annular nozzle, ambient air is drawn through the supplemental air inlet and merges with the flow of high-velocity air exiting the annular nozzle and flows toward the plurality of gamma detectors as cooling air flow.

16. The medical image scanner system of claim 15, wherein the air plenum further comprises an annular airfoil surface located adjacent to and downstream of the annular nozzle.

17. The medical image scanner system of claim 16, further comprising a plurality of fins connecting the air plenum to the annular interior wall.

18. The medical image scanner system claim 17, wherein the plurality of fins maintain a desired spacing between the air plenum and the annular interior wall which forms the supplemental air inlet.

19. The medical image scanner system of claim 15, further comprising a plurality of fins connecting the air plenum to the annular interior wall.

20. The medical image scanner system of claim 19, wherein the plurality of fins maintain a desired spacing between the air plenum and the annular interior wall which forms the supplemental air inlet.

21. The medical image scanner system of claim 15, wherein the air plenum comprises an air inlet for receiving the flow of pressurized air from the remote source.

22. The medical image scanner system of claim 15, wherein the annular interior wall comprises a first annular surface facing the opening of the patient tunnel portion and a second annular surface facing the air plenum and further comprising an annular ridge provided on the second annular surface and located downstream of the annular nozzle.

23. The medical image scanner system of claim 15, wherein the air plenum comprises:
   a cooling air duct portion for carrying the flow of pressurized air, wherein the cooling air duct portion includes the annular nozzle; and
   an exhaust air duct portion for receiving flow of exhaust air and directing the exhaust air away from the medical image scanner, wherein the flow of exhaust air is said cooling air flow after said cooling air flow has flown over the plurality of gamma detectors.

24. The medical image scanner system of claim 15, wherein the ambient air drawn through the supplemental air inlet and merging with the flow of high-velocity air exiting the annular nozzle does not generate additional noise.

25. The medical image scanner system of claim 24, wherein the ambient air drawn through the supplemental air inlet and merging with the flow of high-velocity air exiting the annular nozzle does not generate additional noise due to a lack of a requirement for additional fans or impellers.

26. The medical image scanner system of claim 15, wherein the provision of the remote source for the pressurized air minimizes noise at the medical image scanner system.

27. The medical image scanner system of claim 15, wherein the medical image scanner system further comprises a plurality of remote sources for providing the flow of pressurized air received by the air plenum, whereby the provision of the plurality of remote sources minimizes noise at the medical image scanner system.

28. The medical image scanner system of claim 15, wherein the remote source is distant to the medical image scanner system.

29. The medical image scanner system of claim 15, wherein the remote source comprises at least one of pressurized plant air, one or more fans or one or more impellers.

30. The medical image scanner system of claim 29, wherein the remote source comprising at least two sources allows for the one or more fans to operate at a reduced speed.

31. The medical image scanner system of claim 30, wherein noise is further reduced due to the reduced speed of the one or more fans.

32. The medical image scanner system of claim 15, wherein the remote source is located within the gantry.

33. The medical image scanner system of claim 32, wherein the remote source is provided with sound proofing to minimize noise.

* * * * *